United States Patent
Liu et al.

(10) Patent No.: US 9,051,348 B2
(45) Date of Patent: Jun. 9, 2015

(54) GINSENOSIDE WITH ANTI-CANCER ACTIVITY AND THE PREPARATION METHOD THEREOF

(71) Applicant: Macau University of Science and Technology, Macau (CN)

(72) Inventors: Liang Liu, Macau (CN); Liping Bai, Macau (CN); Hang Dong, Beijing (CN); Kam Wai Wong, Macau (CN); Zhihong Jiang, Macau (CN); Hua Zhou, Macau (CN)

(73) Assignee: Macau University of Science and Technology, Macao (CN)

( * ) Notice: Subject to any disclaimer, the term of this patent is extended or adjusted under 35 U.S.C. 154(b) by 33 days.

(21) Appl. No.: 14/040,738

(22) Filed: Sep. 30, 2013

(65) Prior Publication Data
US 2014/0135278 A1    May 15, 2014

Related U.S. Application Data

(60) Provisional application No. 61/725,997, filed on Nov. 13, 2012.

(51) Int. Cl.
*C07J 17/00* (2006.01)
(52) U.S. Cl.
CPC ................................. *C07J 17/005* (2013.01)
(58) Field of Classification Search
None
See application file for complete search history.

(56) References Cited

PUBLICATIONS

Atopkina et al., Planta Medica, 1999, vol. 65(1), pp. 30-34.*
K. Chan, et al. Cucurbitacin B induces apoptosis and S phase cell cycle arrest in BEL-7402 human hepatocellular carcinoma cells and is effective via oral administration. Cancer Lett 294, 118-24.
J. Liu, et al. 20(R)-ginsenoside Rh2, not 20(S), is a selective osteoclastgenesis inhibitor without any cytotoxicity. Bioorg Med Chem Lett 19, 3320-3 (2009).
H. Dong, et al. The in vitro structure-related anti-cancer activity of ginsenosides and their derivatives. Molecules 16, 10619-10630 (2011).
Y. Gu, et al. Intestinal absorption mechanisms of ginsenoside Rh2: stereoselectivity and involvement of ABC transporters. Xenobiotica 40, 602-12.
R. Kasai, et al. Major Metabolites of Ginseng Sapogenins formed by Rat Liver Microsomes. Chem Pharm Bull 2000, 48, 1226-1227.
P-Y Liao, et al. Dammarane-Type Glycosides from Steamed Notoginseng. J Agric Food Chem 2008, 56, 1751-1756.
NM Duc, et al. Saponins From Vietnamese Ginseng, Panax-Vietnamensis Ha et Grushv Collected in Central Vietnam 2. Chem Pharm Bull 1994, 42, 115-122.
S. Fujita, et al. Dammarane Glycosides from Aerial Part of Neoalsomitra Integrifolola. Phytochemistry 1995, 39, 591-602.
NM Duc, et al. Saponins From Vietnamese Ginseng, Panax-Vietnamensis Ha et Grushv Collected in Central Vietnam 3. Chem Pharm Bull 1994, 42, 634-640.
V. Wong, et al. Mechanistic study of saikosaponin-d (Ssd) on suppression of murine T lymphocyte activation. J Cell Biochem 2009, 107(2):303-15.
V. Wong, al. et al Asian ginseng extract inhibits in vitro and in vivo growth of mouse lewis lung carcinoma via modulation of ERK-p53 and NF-κB signaling. J Cell Biochem 2010, 111(4):899-910.

* cited by examiner

*Primary Examiner* — Traviss C McIntosh, III
(74) *Attorney, Agent, or Firm* — Eagle IP Limited; Jacqueline C. Lui (57) ABSTRACT

The present invention relates to a novel compound derived from ginsenoside Rh2, the preparation methods and the use thereof in treating cancers.

13 Claims, 13 Drawing Sheets

GINSENOSIDE WITH ANTI-CANCER ACTIVITY AND THE PREPARATION METHOD THEREOF

CROSS-REFERENCE TO RELATED APPLICATION

This application claims benefit under 35 U.S.C. §119(e) of U.S. Provisional Application having Ser. No. 61/725,997 filed 13 Nov. 2012, which is hereby incorporated by reference herein in its entirety.

FIELD OF INVENTION

This invention relates to a novel ginsenoside compound derived from ginsenoside Rh2, the preparation methods and the use thereof in treating cancers.

BACKGROUND OF INVENTION

In the past decades, a number of anti-cancer drugs have been discovered from natural products, which represent an attractive source for identification of novel anti-cancer agents [1]. Ginsenoside Rh2 is one of the major ginsenosides of ginseng roots, and previous studies showed that Rh2 could markedly reduce cell proliferation, cause cell cycle arrest and induce differentiation and apoptosis in variety types of cancer cells, of which a number of molecular pathways and proteins are participated in its anti-cancer action. Also, the cytotoxicity of Rh2 ginsenoside against tumor cells showed in different potencies with their stereochemical properties, i.e. 20(R)-Rh2 and 20(S)-Rh2. 20(S)-Rh2 demonstrated potent cytotoxicity against several tumor cell lines, with $IC_{50}$ value of 22-50 µM; while 20(R)-Rh2 is a selective osteoclastgenesis inhibitor but without any cell cytotoxicity [2]. Previous studies of the inventors indicated that 20(S)-Rh2 exhibited cytotoxicity with $IC_{50}$ value of 45-65 µM in a panel of 7 tumor cell lines and also in the human normal lung fibroblasts; while 20(R)-Rh2 only displayed poor solubility without cytotoxic effect up to 100 µM in cell culture. In addition, the inventors have previously demonstrated that the stereochemistry of the hydroxyl group at C-20 of Rh2 ginsenoside plays important roles in anti-tumor activity in vitro [3]. Beside, a recent report revealed that poor intestinal absorption of Rh2 was due to the poor permeability and ABC-transporter-mediated efflux; while the significant stereo-selective absorption of 20(R) isomer exhibited lower absorption profiles possibly due to more potent efflux [4].

SUMMARY OF INVENTION

In light of the foregoing background, it is an object of the present invention to provide an alternative anti-tumor compound.

Accordingly, the present invention, in one aspect, is a ginsenoside compound represented by formula (I):

In another aspect of the present invention, a method of treating cancer is provided, comprising administering an effective amount of aforesaid ginsenoside compound to a subject in need thereof. In an exemplary embodiment, the effective amount ranges from 10-2,000 mg/kg of the ginsenoside compound per dose. In another embodiment, the ginsenoside compound is provided to the subject in need of the treatment through oral administration.

In yet another exemplary embodiment, the cancer is selected from a group consisting of lung cancer, colon cancer, pancreatic cancer, nasopharyngeal carcinoma, liver cancer, breast cancer, prostate cancer, cervical cancer, ovarian cancer, bladder cancer, acute promyelocytic leukemia (APL), acute myeloid leukemia (AML), acute lymphocytic leukemia (ALL), chronic myelogenous leukemia (CML), non-Hodgkin's lymphoma, Hodgkin's disease, chronic lymphocytic leukemia (CLL), myelodysplastic syndrome, Adult T-cell leukemia (ATL), Burkitt's lymphoma, B-cell lymphoma, primary malignant lymphocytes, B-cell chronic lymphocytic leukemia (B-CLL), human THP-1 leukemia and multiple myeloma.

In yet another aspect of the present invention, a use of the ginsenoside compound in the manufacture a chemotherapeutic agent is provided, the chemotherapeutic agent comprises an effective amount of the ginsenoside compound. In an exemplary embodiment, the chemotherapeutic agent is provided to a subject in need thereof via different routes of drug administration, such as intraperitoneal injection, intravenous injection and oral administration.

The present invention, in another aspect, provides a pharmaceutical composition comprising ginsenoside compound of the first aspect of the present invention admixed with a pharmaceutical carrier suitable for use by oral administration.

In another aspect, the present invention provides a method of synthesizing the ginsenoside compound comprising steps of:

a. providing a solution of 20(R)-ginsenoside Rh2;
b. adding mono-persulfate compound and $NaHCO_3$;
c. adding a catalyst solution to the mixture of step (b);
d. standing the catalyzed mixture from step (c) for 8-24 hours at room temperature with magnetic stirring; and
e. purifying the reaction solution of step (d) to obtain said ginsenoside compound.

In an exemplary embodiment, the purifying step (e) further comprises the step of:

i. filtrating the reaction solution of step (d);
ii. removing organic solvents from the filtered solution of step (i) in vacuum; and
iii. loading the reaction solution of step (ii) to an ODS column and eluted with 50% to 90% methanol.

In an exemplary embodiment, the purifying step (e) further comprises the step of:
i. filtrating the reaction solution of step (d);
ii. removing organic solvents from the filtered solution of step (i) in vacuum; and
iii. loading the reaction solution of step (ii) to silica gel column chromatography eluted with chloroform-methanol-water.

In another aspect, the present invention provides a method of synthesizing the ginsenoside compound comprising steps of:
a. preparing a catalyst solution;
b. providing 20(R)-ginsenoside Rh2 in organic solvent;
c. adding the solution of step (b) into the catalyst solution of step (a) and 80% cumene hydroperoxide (CHP) into the mixture thereof;
d. keeping the catalyzed mixture from step (c) for 4-12 hours at 0° C. with stirring;
e. warming said cooled mixture of step (d) to room temperature with stirring for another 40-60 hours; and
f. purifying the reaction solution of step (e) to obtain the ginsenoside compound.

In an exemplary embodiment, the catalyst solution is prepared by:
i. adding $Zr(OtBu)_4$ or $Hf(OtBu)_4$ to a mixture of bishydroxamic acid (BHA), DMPU in THF, DMSO or dioxane; and
ii. cooling the mixture of step (i) to 0° C. after 1 hour of stirring at room temperature.

In another exemplary embodiment, in the step (b), the organic solvent is THF, DMSO, or dioxane. In another exemplary embodiment, the purifying step (f) further comprises the step of:
i. filtrating said reaction solution of step (e);
ii. removing organic solvents from the filtered solution of step (i) in vacuum; and
iii. loading the reaction solution of step (ii) to an ODS column and eluted with 50% to 90% methanol.

In yet an exemplary embodiment, the purifying step (e) further comprises the step of:
i. filtrating the reaction solution of step (e);
ii. removing organic solvents from the filtered solution of step (i) in vacuum; and
iii. loading the reaction solution of step (ii) to silica gel column chromatography eluted with chloroform-methanol-water.

In yet another aspect, the present invention provides a method of synthesizing the ginsenoside compound comprising steps of:
a. preparing a catalyst solution;
b. providing 20(R)-ginsenoside Rh2 in organic solvent;
c. adding said solution of step (b) into said catalyst solution of step (a) and following by 80% CHP;
d. keeping the catalyzed mixture from step (c) for 20-30 hours at room temperature with stirring; and
e. purifying the reaction solution of step (d) to obtain said ginsenoside compound.

In an exemplary embodiment, the catalyst solution is prepared by:
i. adding $VO(O-i-Pr)_3$ to a solution of BHA in THF, DMSO or dioxane; and
ii. stirring the mixture of step (i) for 8 hours at room temperature.

In another exemplary embodiment, in the step (b), the organic solvent is THF, DMSO, or dioxane; the purifying step (e) further comprises the step of:
i. filtrating said reaction solution of step (d);
ii. removing organic solvents from the filtered solution of step (i) in vacuum; and
iii. loading the reaction solution of step (ii) to an ODS column and eluted with 50% to 90% methanol.

In yet an exemplary embodiment, the purifying step (e) further comprises the step of:
i. filtrating the reaction solution of step (d);
ii. removing organic solvents from the filtered solution of step (i) in vacuum; and
iii. loading the reaction solution of step (ii) to silica gel column chromatography eluted with chloroform-methanol-water.

BRIEF DESCRIPTION OF FIGURES

FIGS. 2 (a) and (b) show the result of cell cytotoxicity study of the novel ginsenoside compound toward a panel of cancer cells and normal cells. FIGS. 2 (c) and (d) show the corresponding result of cell cytotoxicity study of 20(S)-Rh2 and 20(R)-Rh2 as control.

FIGS. 3 (a) and (b) show the study result of dose-dependent suppression on the tumor growth of the novel ginsenoside compound.

FIGS. 5 (a) and (b) show the suppressive effect of the novel ginsenoside compound at the treatment groups of 10, 20, 40, and 80 mg/kg/day observed from day 12 to day 21 after oral administration.

FIG. 7 (a) shows the survival rate of the animals treated with the novel ginsenoside compound of the present application studied in Example 4, whereas FIG. 7 (b) shows the change of body weight of the animals studied in Example 4.

DETAILED DESCRIPTION OF THE PREFERRED EMBODIMENTS

As used herein and in the claims, "comprising" means including the following elements but not excluding others.

The following examples are given to enable a skilled person in the art to clearly understand and practice the present invention. Accordingly, a new ginsenoside compound ("the novel compound") is provided that is chemically modified from its parental ginsenoside 20(R)-Rh2, which exhibits specific anti-cancer efficacy in both in vitro and in vivo models. In the in vitro cell culture studies, the novel compound exhibited significant cytotoxicity in a panel of cancer cells, but no cytotoxic effect in normal human lung fibroblasts by using the same range of drug concentrations in cancer cells was observed. Furthermore, the novel compound was found to exhibit potent suppressive effect on the carcinoma growth in LLC-1 bearing C57 mice via oral administration without observable adverse impacts on the major organs and body weight of animals. These results provide solid evidences that the novel compound has potential to be developed as a novel chemotherapeutic agent.

Example 1

Figure 1:
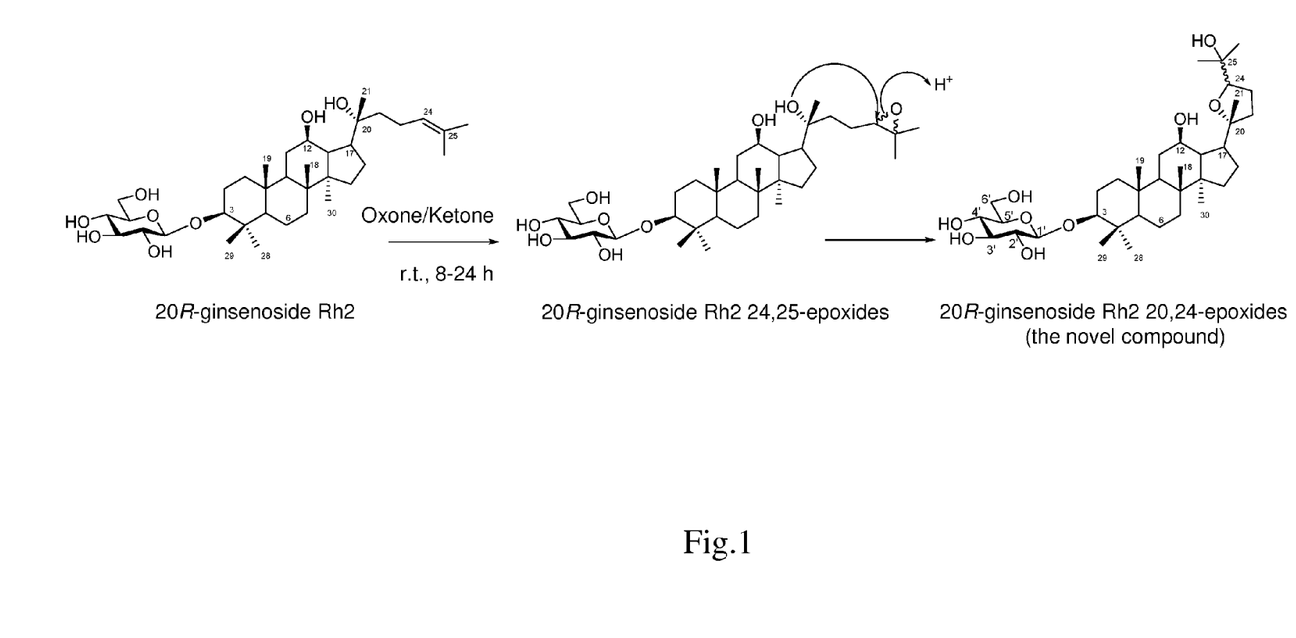
FIG. 1 shows the chemical synthesis and chemical structure of the novel ginsenoside compound according to one embodiment of the present application.

In one embodiment of the present invention, Example 1 describes three methodologies for the organic synthesis of the novel compound from natural ginsenoside 20(R)-Rh2. The chemical synthesis and chemical structure thereof are shown in FIG. 1.

1. Preparation of the Novel Compound

There are three synthetic routes in obtaining the novel compound as discussed below:

1.1 Synthetic Route-1:

A mixture of Oxone® mono-persulfate compound (494.2 mg) and $NaHCO_3$ (210.4 mg) was added slowly to a solution of 20(R)-ginsenoside Rh2 (100 mg) in 60 mL of a 1:1 mixture of acetonitrile and $Na_2$(EDTA) ($4 \times 10^{-4}$ M in water); in one embodiment, acetonitrile can be replaced by methanol or DMSO. Shi epoxidation diketal catalyst (Ketone, 124.5 mg) in 15 mL of acetonitrile was then added dropwise during a period of 10-20 minutes. The reaction mixture was allowed to stand 8-24 hours at room temperature with magnetic stirring. After filtration and removal of organic solvents in vacuum, the reaction solution was directly loaded to an ODS column and eluted with 50% to 90% methanol to obtain the pure novel compound (60-90 mg) of formula (I). The aforesaid synthesis is illustrated in FIG. 1.

Alternatively, the products can also be purified by a silica gel column chromatography eluted with chloroform-methanol-water (from 9:1:0.1 to 7:3:0.5) to obtain the pure novel compound. The total yield by this Synthetic Route-1 was 60-90%.

1.2 Synthetic Route-2:

$Zr(OtBu)_4$ (8.0 μL 0.0200 mmol) or $Hf(OtBu)_4$ (8.0 μL 0.0198 mmol) was added to a mixture of Bishydroxamic Acid (BHA, 0.0202 mmol), DMPU (5.2 mg, 0.0406 mmol) in THF, DMSO or dioxane (1 mL) to prepare a catalyst solution. The catalyst solution was cooled to 0° C. after 1 hour of stirring at room temperature. 20(R)-ginsenoside Rh2 (100 mg, 0.16 mmol) in organic solvents (THF or DMSO, or dioxane) was added to the catalyst solution, followed by 80% cumene hydroperoxide (CHP) (0.26 mL, 1.5 mmol). The reaction mixture was kept stirred at 0° C. for 4-12 hours, warmed to room temperature, and stirred for another 40-60 hours. Afterwards, the solution was purified by ODS or silica gel column chromatography as above mentioned in the Synthetic Route-1 to obtain the pure novel compound of formula (I). The total yield by this Synthetic Route-2 was between 20-50%.

1.3 Synthetic Route-3:

$VO(O-i-Pr)_3$ (0.005 mL, 0.0208 mmol) was added to a solution of BHA (0.0202 mmol) in THF, DMSO or dioxane (0.5 mL), and then stirred for 8 hour at room temperature. 20(R)-ginsenoside Rh2 (100 mg, 0.16 mmol) in organic solvents (THF or DMSO, or dioxane) was added to the aforesaid solution, subsequently followed by 80% CHP (0.5 mL, 3 mmol). The reaction mixture was stirred at room temperature for 20-30 hours until the substrate of 20(R)-ginsenoside Rh2 cannot be detected by TLC. The products were then purified by column chromatography on silica gel or ODS also as mentioned in the Synthetic Route-1 above to obtain the pure novel compound of formula (I). The total yield by this Synthetic Route-3 was around 40-60%.

2. Identification of the Novel Compound:

The novel compound obtained by either of the synthetic routes 1-3 was identified as below: 3-O-β-D-glucopyranosyl 20(R),24-epoxydammarane-3β,12β-triol (i.e. the novel compound): White amorphous powder, optical rotation $[\alpha]_D^{20}$+5.29 (C=0.32, MeOH); High Resolution-ESI-MS (Positive ion mode): m/z 639.4480 [M+H]$^+$ (calculated for $C_{36}H_{63}O_9$: 639.4467); $^1$H-NMR (400 MHz, $C_5D_5N$) δ: 5.04 (2H, d, J=7.8 Hz, H-1'), 4.61 (2H, d, J=11.4 Hz, H-6'a), 4.42 (2H, dd, J=11.4, 5.5 Hz, H-6'b), 4.39 (2H, m, H-3'), 4.23 (2H, m, H-4'), 4.20 (2H, m H-2'), 4.15 (2H, m, H-5'), 4.12 (2H, m, H-24), 3.88 (2H, m, H-12), 3.48 (2H, dd, J=11.7, 4.3, H-3), 1.61, 1.60 (3H each, s, H-27), 1.58, 1.56 (3H each, s, H-21), 1.41, 1.40 (3H each, s, H-26), 1.40, 1.39 (3H each, s, H-18), 1.10 (6H, s, H-28), 1.08, 1.07 (3H each, s, H-30), 1.06, 1.00 (3H each, s, H-19), 0.90 (6H, s, H-29); $^{13}$C-NMR (100 MHz, $C_5D_5N$) δ: 39.7 (C-1), 27.2 (C-2), 89.3 (C-3), 40.2 (C-4), 56.9 (C-5), 19.0 (C-6), 35.8 (C-7), 40.6 (C-8), 50.8 and 50.7 (C-9), 37.6 (C-10), 32.0 and 31.9 (C-11), 71.3 (C-12), 50.2 and 50.1 (C-13), 52.2 and 52.1 (C-14), 32.1 (C-15, 24S-epimer), 31.7 (C-15, 24R-epimer), 27.3 (C-16, 24S-epimer), 27.0 (C-16, 24R-epimer), 51.4 and 51.3 (C-17), 17.0 and 16.9 (C-18), 16.3 and 16.2 (C-19), 86.8 and 86.7 (C-20), 21.9 (C-21, 24R-epimer), 19.6 (C-21, 24S-epimer), 39.8 (C-22, 24R-epimer), 38.7 (C-22, 24S-epimer), 27.5 and 27.4 (C-23), 87.6 (C-24, 24S-epimer) 86.4 (C-24, 24R-epimer), 71.1 (C-25, 24S-epimer), 70.7 (C-25, 24R-epimer), 26.6 and 26.5 (C-26), 28.0 (C-27, 24R-epimer), 27.6 (C-27, 24S-epimer), 28.7 (C-28), 17.4 (C-29), 17.7 and 17.6 (C-30), 107.4 (C-1'), 76.3 (C-2'), 79.3 (C-3'), 72.4 (C-4'), 78.9 (C-5'), 63.6 (C-6').

3. Results:

The oxidation of double bond on the side chain of 20(R)-ginsenoside Rh2 with Oxone/$NaHCO_3$ catalyzed by ketone in the Synthetic Route-1; or, by zirconium or hafnium in the Synthetic Route-2; or by vanacium in the Synthetic Route-3 with BHA ligands, first led to its 24, 25-epoxy compounds, as shown in FIG. 1. The hydroxyl group located at C-20 of these epoxides immediately attacked the electron-demand C-24 to form 20, 24-epoxides in an 1:1 mixture of 24-epimers [5] (checked by UPLC-MS analysis) which was purified by ODS column chromatography (90% methanol). Structure of the novel compound was characterized on the basis of spectroscopic evidence. Its molecular formula $C_{36}H_{62}O_9$ was determined by positive high-resolution ESI-MS. $^1$H-NMR spectrum showed an anomeric proton at δ 5.04 (d, J=7.8 Hz), three oxygenated methine proton signals at δ 4.12 (m), 3.88 (m) and 3.48 (dd, J=11.7, 4.3), and sixteen quaternary methyl groups at δ 1.61, 1.60, 1.58, 1.56, 1.41, 1.40 (6H), 1.39, 1.10 (6H), 1.08, 1.07, 1.06, 1.00, 0.90 (6H). $^{13}$C-NMR spectrum revealed that some signals were in pair indicating the existence of a pair of epimers. The carbon signals at δ 107.4 (C-1'), 76.3 (C-2'), 79.3 (C-3'), 72.4 (C-4'), 78.9 (C-5'), 63.6 (C-6') were assigned to the β-glucopyranosyl moiety of the novel compound [6]. The other carbon signals were almost identical to those of 20R, 24S-epoxy-dammarane-3β-12β, 25-triol and its 24R-epimer by comparison with the literature data [7-9]. The downfield shift of C-3 at δ 89.3 suggested that the glucosyl moiety was attached to C-3 of the aglycone.

4. Conclusion:

The method of chemically synthesizing the novel compound from 20(R)-Rh2 is described herein. The chemical structure thereof was characterized by spectroscopic evidence and UPLC-MS analysis.

Example 2

This example describes the result of in vitro cytotoxicity study in a panel of cancer cells by the novel compound.

1. Cell Culture and Cytotoxicity Assay:

The novel compound was dissolved in DMSO at final concentration of 100 mmol/L and stored at −20° C. Cytotoxicity was assessed using the 3-(4,5-dimethylthiazol-2-yl)-2, 5-diphenyltetrazolium bromide assay as described previously

[10]. Several kinds of cells were seeded on 96-well plates, namely MCF-7, 4000 cells; HepG2, 4000 cells; HeLa, 3000 cells; A549, 4000 cells; LLC-1, 3000 cells; H1299, 3000 cells; CCD19Lu, 4000 cells per well. After overnight pre-incubation, the cells were exposed to different concentrations of the novel compound (0.039-100 μmol/L) or control compounds 20(S)-Rh2 and 20(R)-Rh2 for 3 days. Subsequently, 10 μL of MTT reagents was added to each well and incubated at 37° C. for 4 hours followed by the addition of 100 μL solubilization buffer (10% SDS in 0.01 mol/L HCl) and overnight incubation. $A_{585\,nm}$ was determined from each well the next day. The percentage of viable cells was calculated using the following formula: Cell viability (%)=$A_{treated}/A_{control}$× 100. Data was obtained from three independent experiments.

Figure 2A:
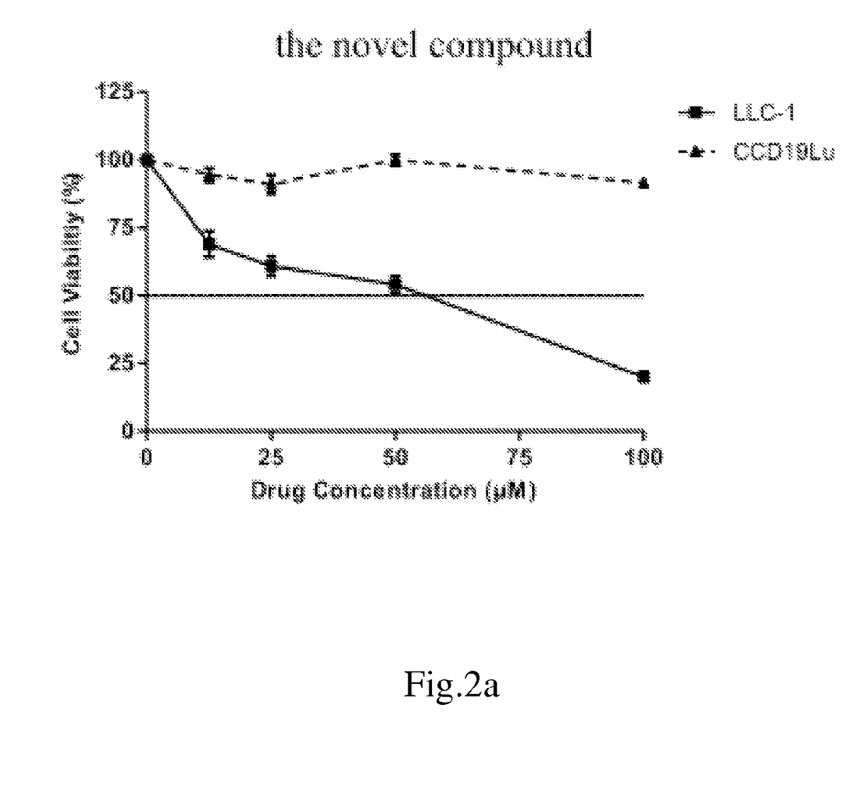
Figure 2B:
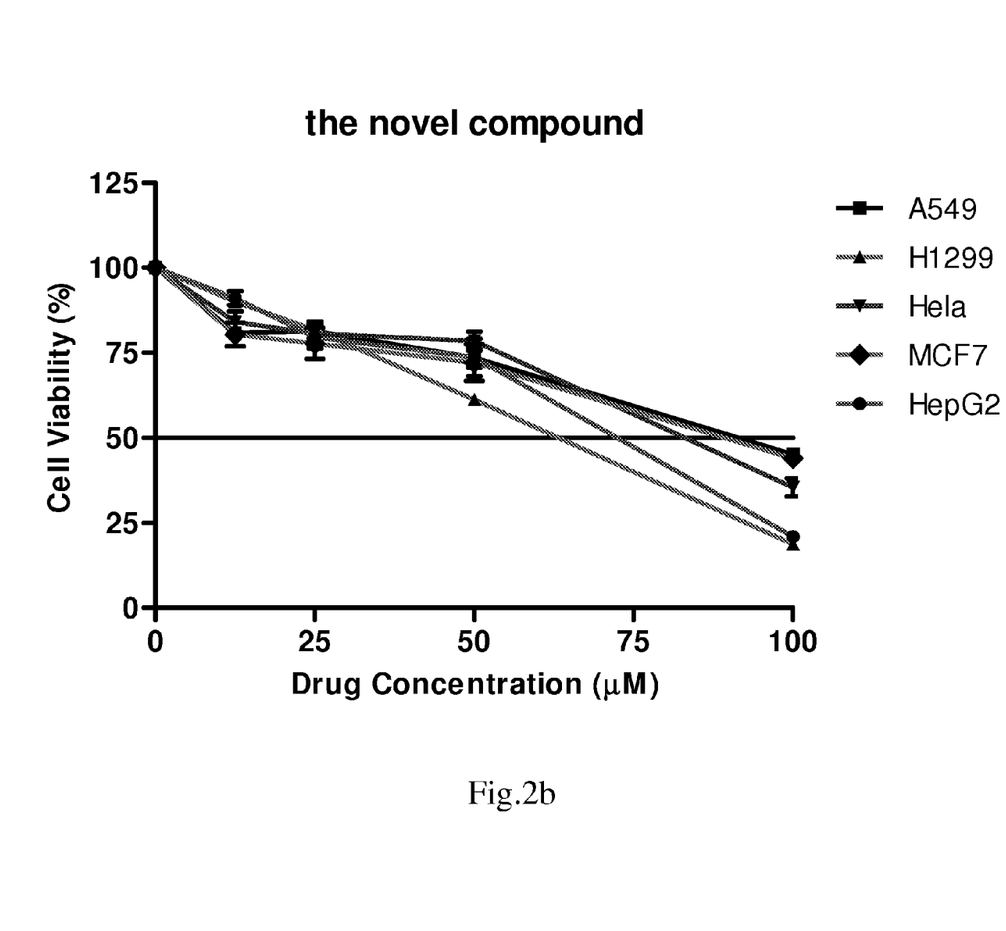
Figure 2C:
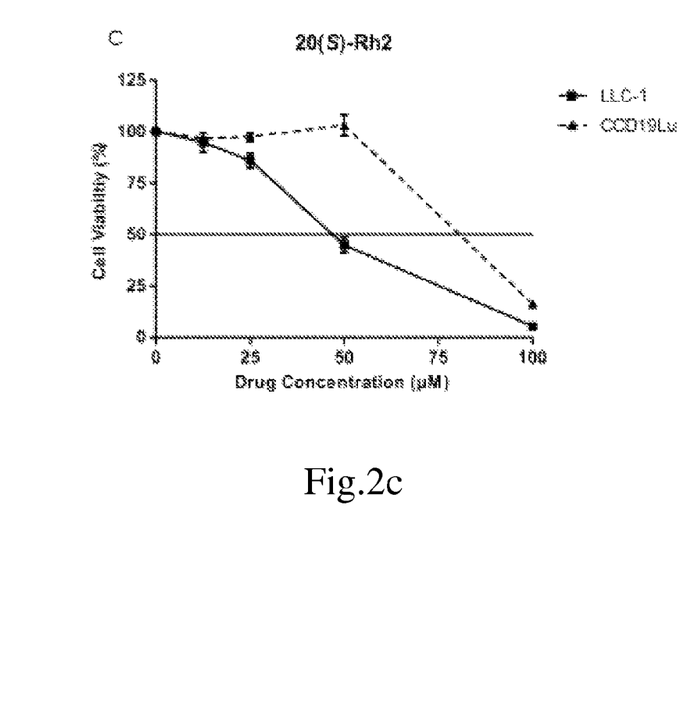
Figure 2D:
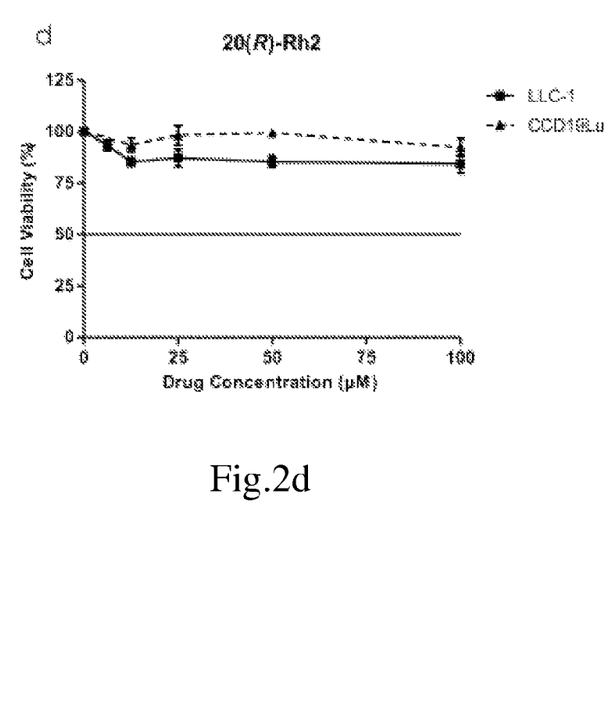

2. Results:

As shown in FIG. 2a, the novel compound has a significant cytotoxic effect on lung cancer cells (LLC-1) with $IC_{50}$ of 56 μM, but without marked impairment to human normal lung fibroblasts CCD19Lu under the drug concentration of over 100 μM. The novel compound also displayed dose-dependent cytotoxic potency against other five cancer cell lines with different genetic backgrounds, as shown in FIG. 2b. For structure-activity comparison of the two subtypes of the natural Rh2 ginsenoside, 20(S)-Rh2 displayed its cytotoxicity in both LLC-1 and CCD19Lu cells, with $IC_{50}$ of 46.5 μM and 80.5 μM, respectively, while 20(R)-Rh2 exhibited no cytotoxicity in both LLC-1 and CCD19Lu cells, as shown in FIGS. 2c & d.

3. Conclusion:

Structure modification on the non-effective natural ginsenoside 20(R)-Rh2 successfully leads to production of a novel compound, which exhibits specific cell cytotoxicity toward a panel of cancer cells but non-toxic to normal human cells and tissues.

Example 3

This example describes an animal study to demonstrate that oral administration of the novel compound is useful in suppression of tumor growth in vivo.

1. Xenograft Model and Oral Administration Protocol [11]:

The LLC-1 cells harvested from in vitro culture were adjusted to a concentration of 1.5×10$^7$/mL and 0.1 mL cell suspension was injected subcutaneously into the dorsal region of the male C57BL/6J mice. Subsequently, when 70% of mice had developed tumor into a volume (length×width$^2$× 0.52) larger than 50 mm$^3$, the animals were randomly divided into the vehicle control and several treatment groups. The novel compound powder was dissolved with PEG400:ethanol:distilled water in a ratio of 60%:10%:30% (v/v/v), and orally administrated to mice by gavage feeding at doses of 10, 20, 40 and 80 mg/kg/day for 21 consecutive days. Oral administration of 80 mg/kg/day 20(R)-Rh2, 20(S)-Rh2 and 20(S)-Rg3, and 10 mg/kg/day 5-Fu were designed as control groups. In order to make sure all groups were appropriately blended, all the experimental procedures such as subcutaneous tumor cells injection, treatment and tumor size measurement were performed by three individual persons who were blended for animal group identity.

Figure 3A:
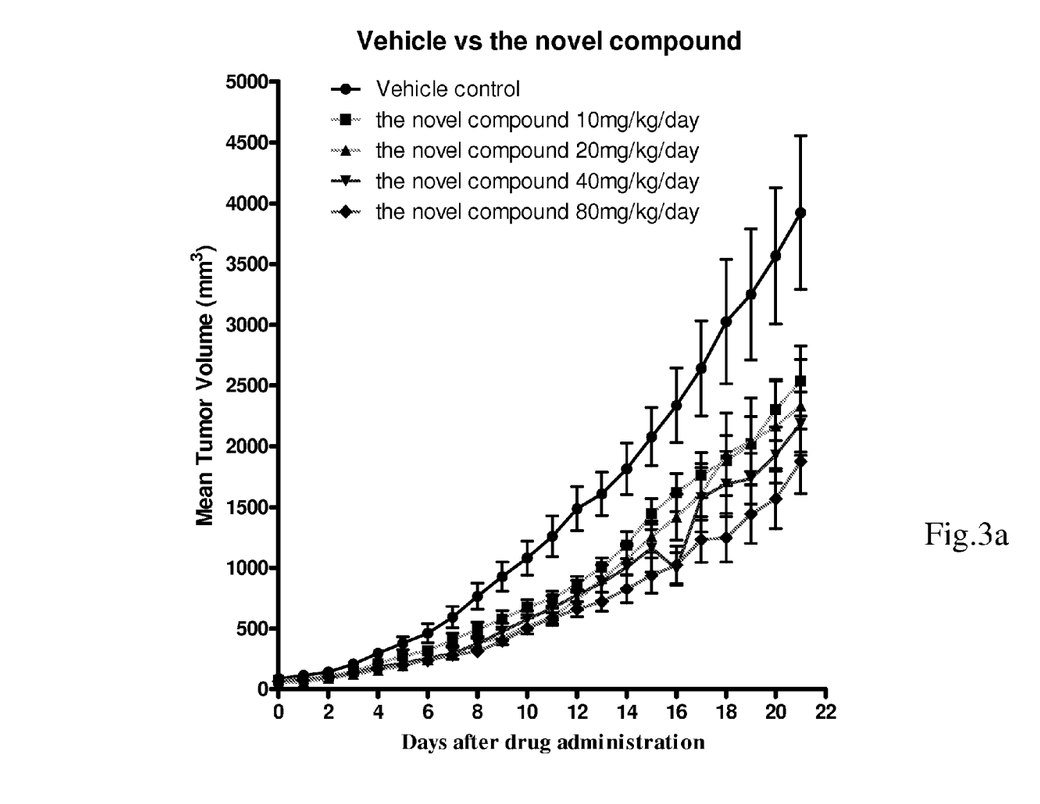
Figure 3B:
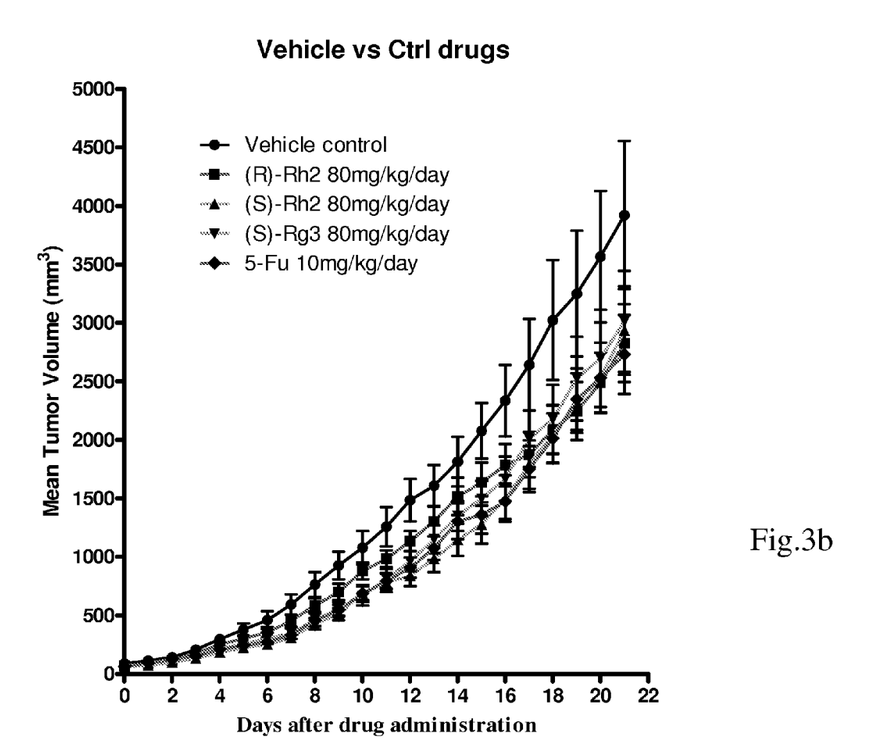
Figure 4:
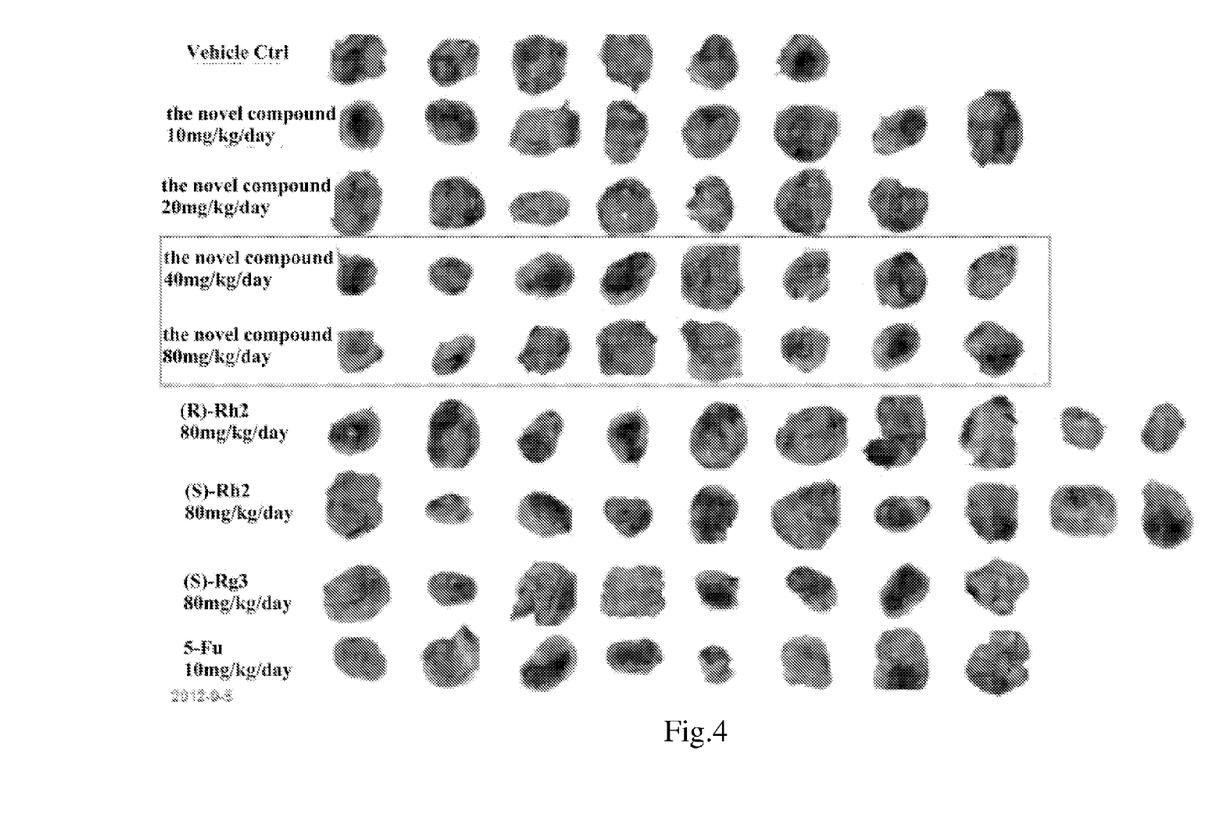
FIG. 4 shows the study result of dose-dependent suppression on the tumor growth of the novel ginsenoside compound.
Figure 5A:
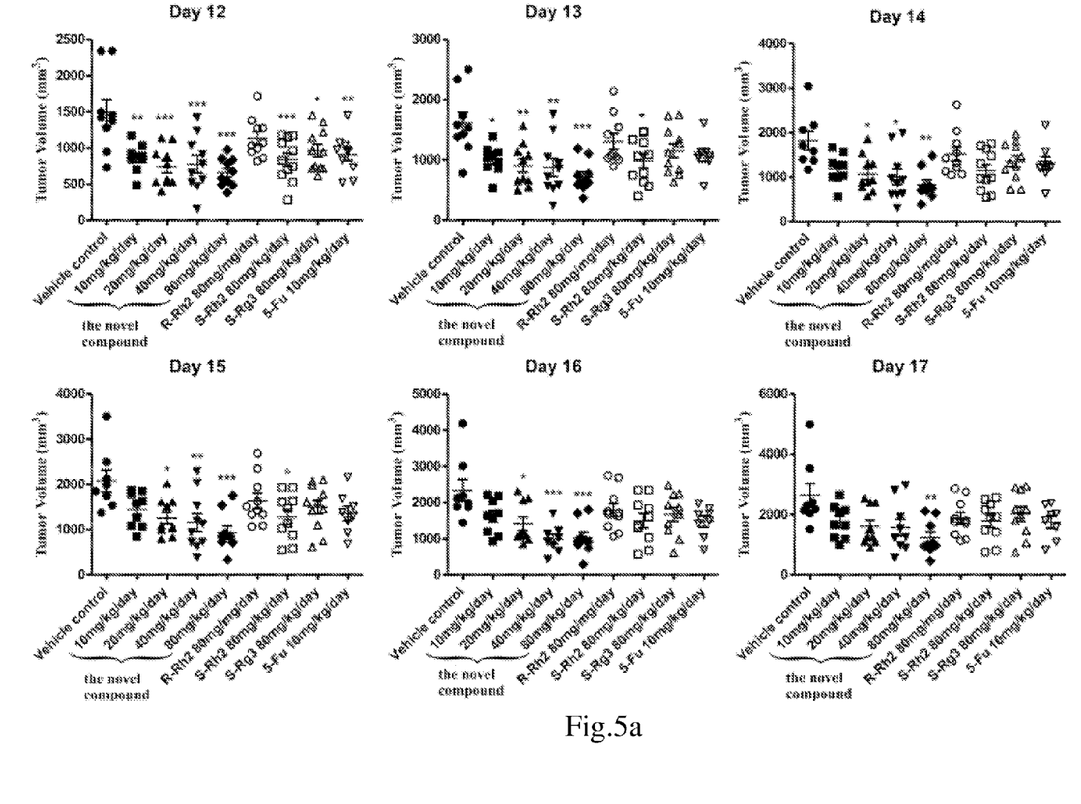
Figure 5B:
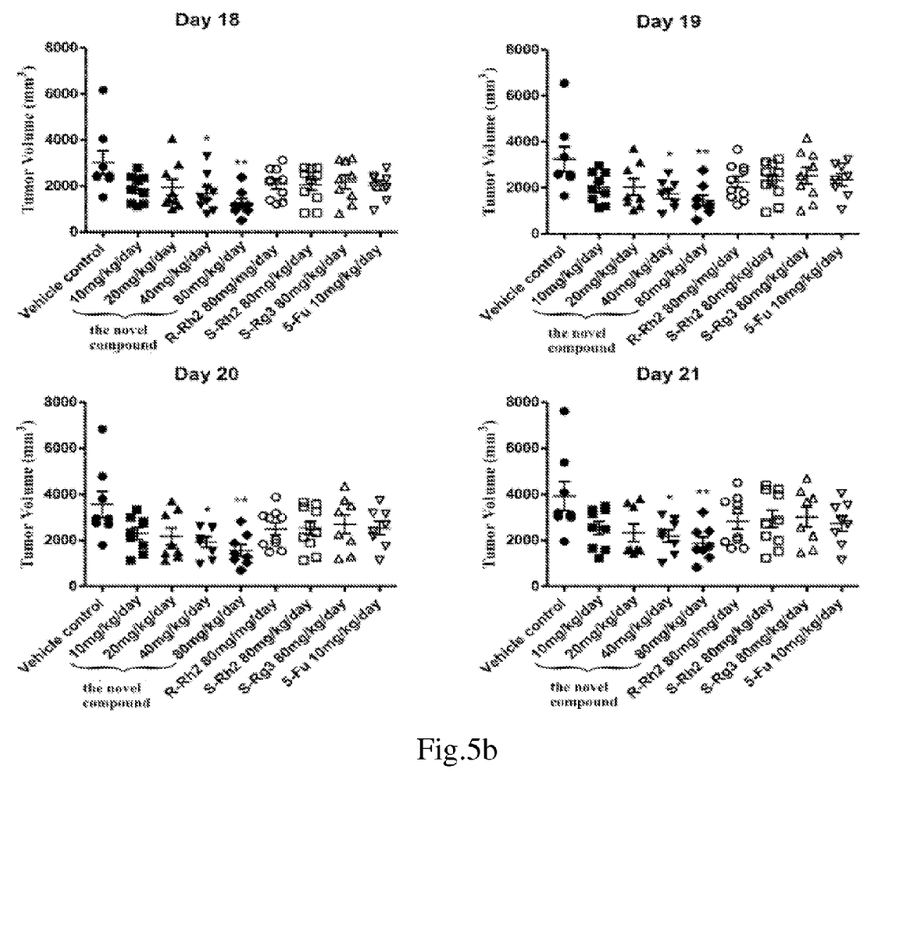
Figure 6A:
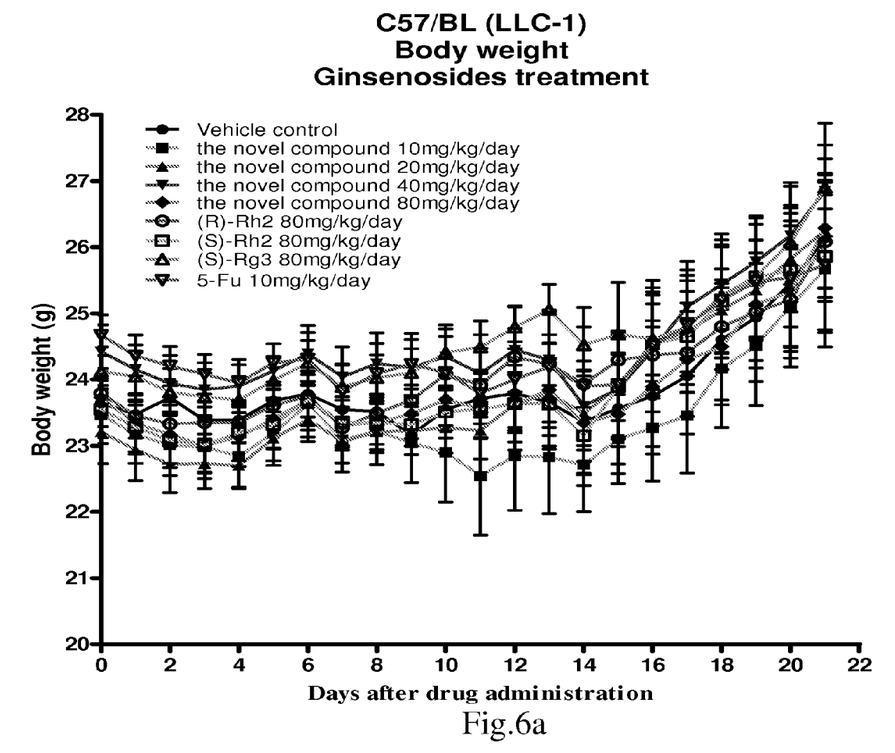
FIGS. 6(a) and (b) show the change of body weight of the animals in Example 3.
Figure 6B:
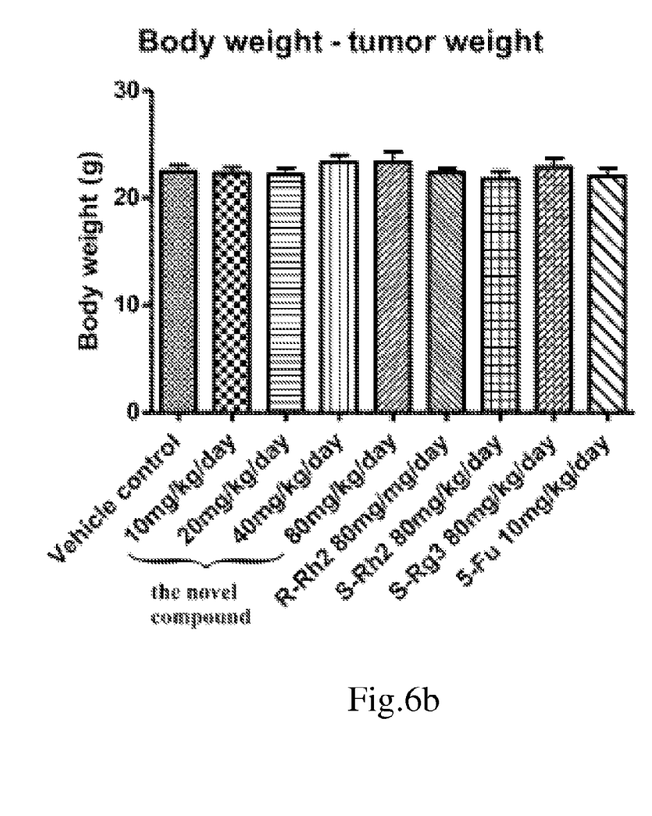

2. Results:

Oral administration of the novel compound at dosages of 10, 20, 40 and 80 mg/kg/day demonstrated significant and dose-dependent suppression on the tumor growth, up to 35.24% (P>0.05), 40.49% (P>0.05), 44.9% (P<0.05) and 52.04% (P<0.01), respectively, after a 21-day treatment course as compared to the mice treated by the vehicle (as shown in FIGS. 3 & 4). The suppressive effect of the novel compound at the treatment groups of 40 and 80 mg/kg/day were significantly observed from day 12 to day 21 after oral administration (as shown in FIGS. 5 (a) & (b)). Moreover, it was noted that there was no significant difference in body weights between the vehicle control and the novel compound-treated group after deduction of the solid tumors weight of each animal in all of the groups (see FIGS. 6 (a) & (b)).

3. Conclusion:

The novel compound at dosages of 40 and 80 mg/kg/day exhibit significant tumor suppressive effect in tumor growth in mice via oral administration without affecting the body weight.

Example 4

This example describes sub-chronic lethal dose study of the novel compound in which oral administration of the novel compound in high dosages is not harmful to mice in 7-day repeated dosing.

1. Animal Model and Oral Administration Protocol:

10 male C57BL/6J mice were divided into two treatment groups, i.e. 160 mg/kg/day and 320 mg/kg/day. The novel compound powder was dissolved with PEG400:ethanol:distilled water in a ratio of 60%:10%:30% (v/v/v), and orally administrated to mice by gavage feeding at doses of 160 and 320 mg/kg/day for 7 consecutive days. The health condition of the animals was monitored and their body weights were recorded during this 7 days treatment duration.

Figure 7A:
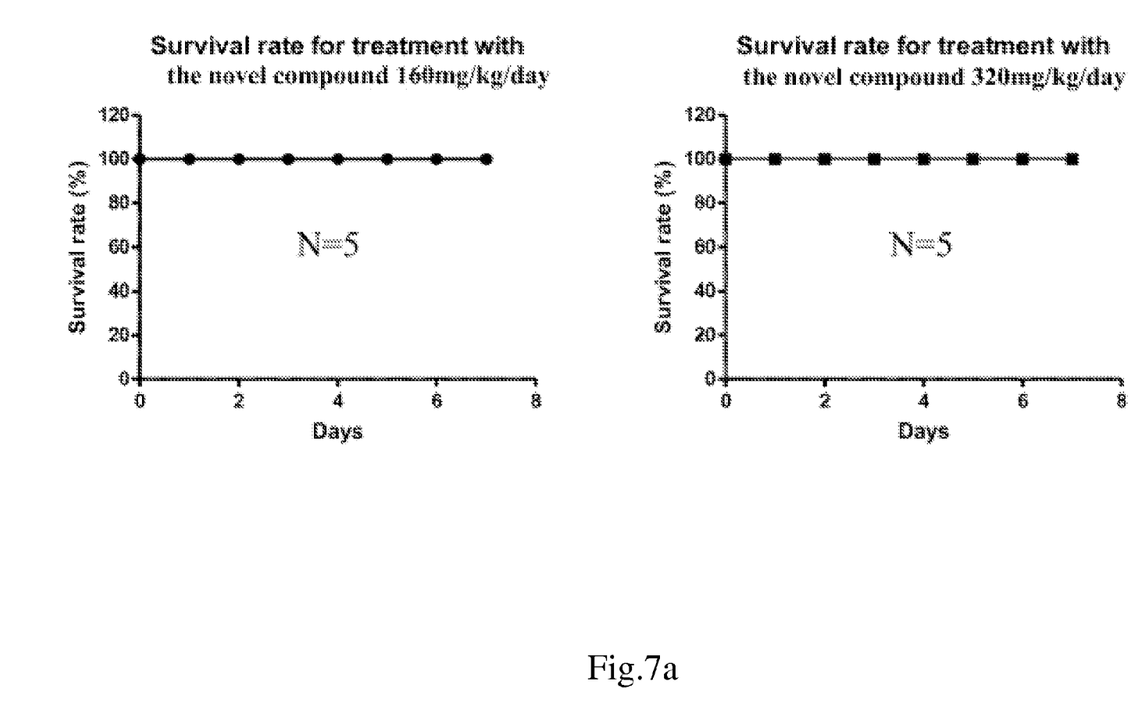
Figure 7B:
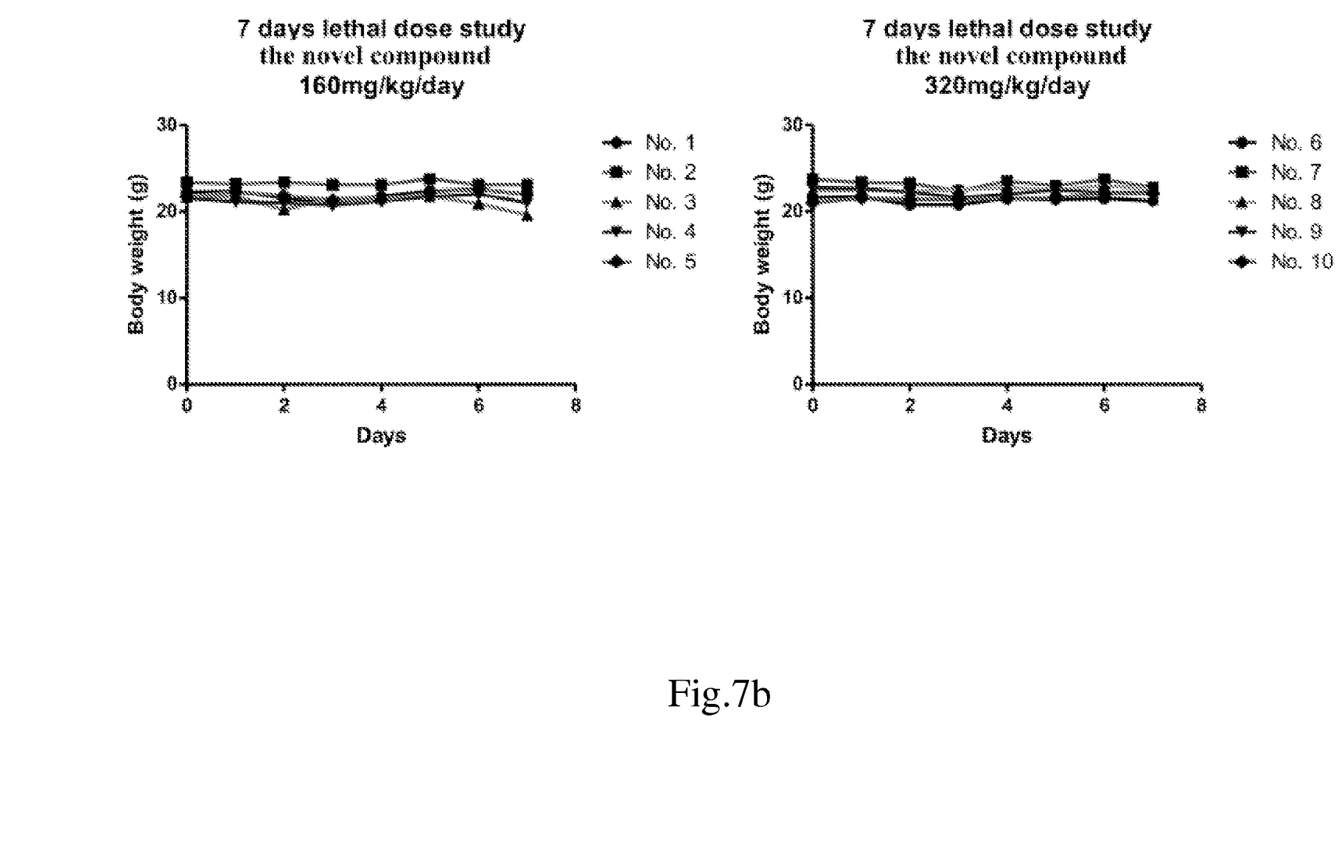

2. Results:

As shown in FIGS. 7 (a) to (b), oral administration of the novel compound at dosages of 160 and 320 mg/kg/day were not harmful to the animal that 100% of animal survived and no significant drop of body weight was encountered after a 7-day treatment course.

3. Conclusion:

The novel compound derived from 20(R)-Rh2 is non-toxic to mice up to 320 mg/kg/day for 7 days by oral administration.

Example 5

This example describes acute oral toxicity in 14-day lethal dose study of the novel compound in which oral administration of the novel compound at 2000 mg/kg is not harmful to mice in 14 days after single dosing.

1. Methods and Results:

The acute oral toxicity of the novel compound was evaluated in line with the Organization for Economic Cooperation and Development (OECD) Guideline for Testing Chemicals—Acute Oral Toxicity—Acute Toxic Class Method (Test Guideline 423, Adopted on 17 Dec. 2001). Based on the result of Example 4, the Test Procedure with a Starting Dose of 2000 mg/kg (Annex 2d of OECD 423) was selected to evaluate the acute toxicity of the novel compound. In the test, 3 female and 3 male C57BL/6J mice (SPF grade) were fasted overnight and then orally administrated by gavage feeding with single dose of the novel compound solution at 2000 mg/kg. The mortality and health condition of the animals were monitored for 14 days and the result showed zero animal death in both gender. In addition, no significant drop of body weight and sign of toxicity were observed.

Based on the testing principle and evaluation criteria of OECD Test Guideline 423, the novel compound can be classified as Class 5 or unclassified under Globally Harmonized Classification System (GHS) and the $LD_{50}$ of the novel compound is estimated larger than 5000 mg/kg.

2. Conclusion:

The novel compound is non-toxic to mice after single dosing at 2000 mg/kg oral administration and the $LD_{50}$ of the novel compound is classified as >5000 mg/kg.

The exemplary embodiments of the present invention are thus fully described. Although the description referred to particular embodiments, it will be clear to one skilled in the art that the present invention may be practiced with variation of these specific details. Hence this invention should not be construed as limited to the embodiments set forth herein.

REFERENCES

1. Chan, K. T. et al. Cucurbitacin B induces apoptosis and S phase cell cycle arrest in BEL-7402 human hepatocellular carcinoma cells and is effective via oral administration. Cancer Lett 294, 118-24.
2. Liu, J. et al. 20(R)-ginsenoside Rh2, not 20(S), is a selective osteoclastgenesis inhibitor without any cytotoxicity. Bioorg Med Chem Lett 19, 3320-3 (2009).
3. Dong, H. et al. The in vitro structure-related anti-cancer activity of ginsenosides and their derivatives. Molecules 16, 10619-10630 (2011).
4. Gu, Y. et al. Intestinal absorption mechanisms of ginsenoside Rh2: stereoselectivity and involvement of ABC transporters. Xenobiotica 40, 602-12.
5. Kasai, R, Hara K, Dokan R, Suzuki N, Mizutare T, Yoshihara S, Yamasaki K, Chem Pharm Bull 2000, 48, 1226-1227.
6. Liao P-Y, Wang D, Zhang Y-J, Yang C-R, J Agric Food Chem 2008, 56, 1751-1756.
7. Duc N M, Kasai R, Ohtani K, Ito A, Nham, N T, Yamasaki K, Tanaka O, Chem Pharm Bull 1994, 42, 115-122.
8. Fujita S, Kasai R, Ohtani K, Yamasaki K, Chiu M-H, Nie R-L, Tanaka O, Phytochemistry 1995, 39, 591-602.
9. Duc N M, Kasai R, Ohtani K, Ito A, Nham N T, Yamasaki K, Tanaka O, Chem Pharm Bull 1994, 42, 634-640.
10. Wong V K, Zhou H, Cheung S S, Li T, Liu L. Mechanistic study of saikosaponin-d (Ssd) on suppression of murine T lymphocyte activation. J Cell Biochem 2009, 107(2):303-15.
11. Wong V K, Cheung S S, Li T, Jiang Z H, Wang J R, Dong H, Yi X Q, Zhou H, Liu L. Asian ginseng extract inhibits in vitro and in vivo growth of mouse lewis lung carcinoma via modulation of ERK-p53 and NF-κB signaling. J Cell Biochem 2010, 111(4):899-910.

What is claimed is:

1. A ginsenoside compound wherein said compound is represented by formula (I)

2. A method of treating cancer comprising administering an effective amount of said ginsenoside compound of claim 1 to a subject in need thereof.

3. The method according to claim 2 wherein said effective amount ranges from 10-2,000 mg/kg of said ginsenoside compound per dose.

4. The method according to claim 2, wherein said cancer is selected from a group consisting of lung cancer, colon cancer, pancreatic cancer, nasopharyngeal carcinoma, liver cancer, breast cancer, prostate cancer, cervical cancer, ovarian cancer, bladder cancer, acute promyelocytic leukemia (APL), acute myeloid leukemia (AML), acute lymphocytic leukemia (ALL), chronic myelogenous leukemia (CML), non-Hodgkin's lymphoma, Hodgkin's disease, chronic lymphocytic leukemia (CLL), myelodysplastic syndrome, Adult T-cell leukemia (ATL), Burkitt's lymphoma, B-cell lymphoma, primary malignant lymphocytes, B-cell chronic lymphocytic leukemia (B-CLL), human THP-1 leukemia and multiple myeloma.

5. A pharmaceutical composition comprising ginsenoside compound according to claim 1 admixed with a pharmaceutical carrier suitable for use by oral administration.

6. A method of synthesizing ginsenoside compound according to claim 1 comprising the steps of:
   a. providing a solution of 20(R)-ginsenoside Rh2;
   b. adding mono-persulfate compound and $NaHCO_3$;
   c. adding a catalyst solution to the mixture of step (b);
   d. standing the catalyzed mixture from step (c) for 8-24 hours at room temperature with magnetic stirring; and
   e. purifying the reaction solution of step (d) to obtain said ginsenoside compound.

7. The method according to claim 6 wherein said purifying step (e) further comprises the step of:
   a) filtrating said reaction solution of step (d);
   b) removing organic solvents from the filtered solution of step (i) in vacuum; and
   c) loading the reaction solution of step (ii) to an ODS column and eluted with 50% to 90% methanol.

8. The method according to claim 6 wherein said purifying step (e) further comprises the step of:
   a) filtrating said reaction solution of step (d);
   b) removing organic solvents from the filtered solution of step (i) in vacuum; and
   c) loading the reaction solution of step (ii) to silica gel column chromatography eluted with chloroform-methanol-water.

9. A method of synthesizing ginsenoside of claim 1 comprising steps of:
   a. preparing a catalyst solution;
   b. providing 20(R)-ginsenoside Rh2 in organic solvent;
   c. adding said solution of step (b) into said catalyst solution of step (a) and 80% cumene hydroperoxide into the mixture thereof;
   d. keeping said catalyzed mixture from step (c) for 4-12 hours at 0° C. with stirring;
   e. warming said cooled mixture of step (d) to room temperature with stirring for another 40-60 hours; and
   f. purifying the reaction solution of step (e) to obtain said ginsenoside compound.

10. The method according to claim 9 wherein said catalyst solution is prepared by:
   i. adding $Zr(OtBu)_4$ or $Hf(OtBu)_4$ to a mixture of bishydroxamic acid, DMPU in THF, DMSO or dioxane; and
   ii. cooling the mixture of step (i) to 0° C. after 1 hour of stirring at room temperature.

11. The method according to claim 9 wherein in said step (b), said organic solvent is THF, DMSO, or dioxane.

12. The method according to claim 9 wherein said purifying step (f) further comprises the step of:
   a) filtrating said reaction solution of step (e);
   b) removing organic solvents from the filtered solution of step (i) in vacuum; and
   c) loading the reaction solution of step (ii) to an ODS column and eluted with 50% to 90% methanol.

13. The method according to claim 9 wherein said purifying step further comprises the step of:
   a) filtrating said reaction solution of step (e);
   b) removing organic solvents from the filtered solution of step (i) in vacuum; and
   c) loading the reaction solution of step (ii) to silica gel column chromatography eluted with chloroform-methanol-water.

* * * * *